United States Patent [19]

Rubinstein et al.

[11] Patent Number: 5,789,147
[45] Date of Patent: Aug. 4, 1998

[54] METHOD FOR CONCENTRATING WHITE CELLS FROM WHOLE BLOOD BY ADDING A RED CELL SEDIMENTATION REAGENT TO WHOLE ANTICOAGULATED BLOOD

[75] Inventors: Pablo Rubinstein, New Rochelle, N.Y.; Philip Henry Coelho, El Dorado Hills, Calif.; Cladd E. Stevens, New York, N.Y.

[73] Assignee: New York Blood Center, Inc., New York, N.Y.

[21] Appl. No.: 349,747

[22] Filed: Dec. 5, 1994

[51] Int. Cl.$^6$ .............................. A01N 1/02; A01N 63/00; A61B 19/00
[52] U.S. Cl. ..................... 435/2; 424/93.7; 424/93.71; 604/410; 604/416
[58] Field of Search ............................ 435/2; 424/93.7, 424/93.71

[56] References Cited

U.S. PATENT DOCUMENTS

| | | | |
|---|---|---|---|
| 2,702,034 | 2/1955 | Walter | 128/214 |
| 3,187,750 | 6/1965 | Tenczar, Jr. | 128/272 |
| 4,004,975 | 1/1977 | Lionetti et al. | 195/1.8 |
| 4,332,122 | 6/1982 | Williams | 53/425 |
| 4,343,793 | 8/1982 | Wissler | 424/101 |
| 4,744,907 | 5/1988 | Klimchak | 210/730 |
| 4,937,194 | 6/1990 | Pattillo et al. | 435/240.2 |
| 5,004,681 | 4/1991 | Boyse et al. | 435/2 |
| 5,104,788 | 4/1992 | Carmen et al. | 435/2 |
| 5,154,716 | 10/1992 | Bauman et al. | 604/410 |
| 5,192,553 | 3/1993 | Boyse et al. | 424/529 |
| 5,397,479 | 3/1995 | Kass et al. | 210/728 |

OTHER PUBLICATIONS

Rubinstein P. et al, PNAS 92:10119–22 (1995).
Korbling, et al. *Transfusion* vol. 20, No. 3, pp. 293–300 (1960).
Pablo Rubinstein, Richard E. Rosenfield, John W. Adamson and Cladd E. Stevens (The Lindsley F. Kimball Research Institue of The New York Blood Center); *Stored Placental Blood for Unrelated Bone Marrow Reconstitution*; May, 1993; entire paper.

*Primary Examiner*—Sandy Saucier

[57] ABSTRACT

A therapeutic product formed from a high concentration of white blood cells having a high degree of cell viability. The white blood cells are sequestered from their normal population presence in whole blood by placing the blood into a container and preventing coagulation of the blood, separating the blood into two components, one of which is extremely rich in white blood cells through the use of a reagent and centrifugation, sequestering the white cell concentration, and freezing the white cells.

9 Claims, 3 Drawing Sheets

METHOD FOR CONCENTRATING WHITE CELLS FROM WHOLE BLOOD BY ADDING A RED CELL SEDIMENTATION REAGENT TO WHOLE ANTICOAGULATED BLOOD

FIELD OF THE INVENTION

The following invention is directed generally to the therapeutic utilization of white blood cells, a technique for sequestering the white blood cells by causing them to coalesce in a population density greater than they normally occur in nature, and a method for causing an enriched concentration in conjunction with an array of bags oriented in a set that facilitates both the concentration process and a method for preserving the white blood cells.

BACKGROUND OF THE INVENTION

It is now recognized that placenta/umbilical cord blood (PB) contains large numbers of hematopoietic stem and progenitor cells that endow PB with extraordinary therapeutic capabilities in the reconstitution of bone marrow damaged as a result of inherited diseases, accidents or medical procedures. As in the case of ordinary collection of bone marrow for transplantation, PB contains immune cells potentially capable of mounting specific responses against the recipients of such transplants, but in contrast to adult immunological cells, those in PB display a lower, perhaps much lower tendency to produce damaging immune responses against the recipient. The clinical syndrome produced by the immuno responses of the graft against the recipient's cells and tissues is designated "Graft versus Host Disease" (GVHD). In the typical clinical situation, the recipient's own immune response against the graft is abrogated by drugs and irradiation treatments designed to reduce or eliminate the immunological and other hematopoietic cells and thus avoid the host versus graft immune reaction that would cause rejection of the graft. It has been proven that the principal targets of these Graft versus Host and Host versus Graft immune reactions are antigens encoded by the genes of the HLA (Human Leukocyte Antigen) system and that successful outcomes of bone marrow transplants are dependent on the sharing of HLA antigens by donor and recipient. Sibling donors who have inherited the same paternal and maternal HLA genes present in the recipient are HLA-identical and thus, optimal from this viewpoint. Patients lacking such HLA-identical sibling donors must receive transplants from more distant relatives or from unrelated donors. Because the HLA system includes several discrete genes each of which displays an extremely large number of antigenically different variants in the population, such distant relative-donor or unrelated-donor transplants must be expected to contain a variable number of HLA incompatibilities unless they are selected from among potential donors by identifying the specific variants present in each and choosing donors whose HLA antigens match those of the recipient. To perform this selection with significant probability of success, it is necessary to have access to large panels of potential donors whose HLA antigens are known. In the case of unrelated donor PB, this requires establishing a bank of frozen HLA-typed units collected from random placentas. Heretofore, the most widely accepted method for freezing PB consisted of adding to the whole PB unit an equal volume of a cryopreservative solution, with the double disadvantage that the volume of each cryopreserved unit becomes very large and that a relatively large amount of possibly deleterious cryopreservative is eventually administered to the recipients of such PB units. Administration of cryoprotectant and hemoglobin from erythrocytes destroyed by using a freezing and thawing method designed to protect the stem and progenitor cells but not the erythrocytes may have toxic effects generally and especially on specific organs such as the kidney of the recipient. In addition, there is the logistical consequence that a large number of freezers would be needed to contain useful numbers of the large volume frozen units in reserve, with the attending increase in up-front and running costs. The applicants have developed a practical method that allows a substantial reduction of the volume of PB Units by eliminating the unneeded mature red blood cells and an equivalent volume of plasma. This submission describes this method and a specially designed set of plastic bags and connecting tubes intended to facilitate the accomplishment of the desired concentration of the needed stem cells and progenitor cells with minimal manipulation and risk of contamination. Essentially, this method will allow an experimental, time consuming laboratory process to become a routine procedure in blood banks.

The following submission reflects the state of the art of which applicant is aware insofar as these documents appear germane to the patent process. However, it is respectfully stipulated that none of these patents teach singly nor render obvious when considered in any conceivable combination the nexus of the instant invention as set forth hereinafter.

| INVENTOR | PATENT NO. | ISSUE DATE |
| --- | --- | --- |
| Tenczar, Jr. | 3,187,750 | 06/1965 |
| Williams | 4,332,122 | 06/1982 |
| Pattillo, et al. | 4,937,194 | 06/1990 |
| Boyse, et al. | 5,004,681 | 04/1991 |
| Carmen, et al. | 5,104,788 | 04/1992 |
| Bauman, et al. | 5,154,716 | 10/1992 |
| Boyse, et al. | 5,192,553 | 03/1993 |

OTHER PRIOR ART (Including Author, Title, Date, Pertinent Pages, Etc.)

Pablo Rubinstein, Richard E. Rosenfield, John W. Adamson and Cladd E. Stevens (The Lindsley F. Kimball Research Institute of The New York Blood Center); *Stored Placental Blood for Unrelated Bone Marrow Reconstitution*; May, 1993; entire paper.

SUMMARY OF THE INVENTION

The therapeutic product of the present invention is advantageous, first, because it recovers all or almost all of the stem and progenitor cells of the original collection of PB in a small and uniform volume that requires minimal and predictable storage space, second, because it permits a consistent methodology for processing PB units which results in a routinely dependable product with less dependence on operator skill and third, because the potentially deleterious effects of the cryoprotectant and of the free hemoglobin are minimized.

One first aspect to the nature of the product improved according to the present invention involves the methodology by which the white blood cells (which include the hematopoietic stem and progenitor cells) are separated from the bulk of other components in the whole PB and the manner in which the viability of such white cells is preserved by avoiding exposure to bacterial and fungal contamination, potentially damaging chemical agents, excessive centrifugal forces and osmotic imbalances. Typically, bacterial and/or fungal contamination occurs when PB or white blood cell suspensions derived from PB are exposed to ambient air in the course of preparatory manipulations; chemical damage is possible when certain chemicals are used to lyse the accompanying red blood cells or to aggregate white cells; and physical damage follows the use of excessive centrifugal speed in separation of the cellular components of the blood according to their density, by centrifugal stratification. In addition, the method according to the present invention provides for avoidance of prolonged exposure of the separated white blood cells to cryopreservation solutions at room temperature, an exposure that results in decreased viability of the white blood cells and of the stem and progenitor cells contained therein because of osmotic imbalances and, possibly, other toxic effects of the intracellular cryoprotectants themselves.

Another aspect of the present invention involves the set of interconnected plastic containers (designated as bags). The set under the present invention permits a selective concentration of the white blood cells and of the stem and progenitor cells contained therein without reducing their normally high viability and freedom from contamination by infectious organisms from the environment. Whole PB is collected into a mother bag and is subsequently processed through a series of bags of appropriate chemical structure and physical shape and capacity culminating in storage of a separated fraction containing most of the white blood cells of the collected PB in liquid nitrogen at −196° C. inside a specially constructed freezer bag. Intervening steps include the addition of substances that enhance the alterability of red blood cells and the separation of components by transferring supernatants into connected satellite bags. A special bag and its connecting assembly permits the addition of measured amounts of cryoprotectant to the separated white blood cell concentrate. This connecting assembly allows the cryoprotectant to be added to the white cells at a precise, slow speed required to maintain optimal cell viability.

The bag which is to be used for freezing and storage includes a plurality of connected, but detachable compartments for sequestration of the white blood cells into different discrete chambers. One chamber, the main compartment, is intended to keep the bulk of the white blood cells. A smaller compartment lends itself to the storage of a smaller fraction of the bag contents which may be separated from the main compartment without thawing, and extemporaneously detached from it for separate thawing and subsequent in vitro expansion of the hematopoietic stem and progenitor cell populations contained in the corresponding fraction of the white blood cells. A third and subsequent chamber contains very small aliquots of the white blood cell suspension and are intended to serve as detachable samples for testing the aptness of the unit to be transplanted or assessing its suitability as donor tissue for a specific recipient. The freezing bag also includes indicia on the outer surface of each of its detachable areas for identification of the specific unit that will be stored in it, to facilitate storage and retrieval from designated sectors of cryogenic storage depots. Means are also provided in an exterior surface of the freezer bag to facilitate the placing and removing of the freezer bag into and from, respectively, its assigned storage location by automated instrumentation.

OBJECTS OF THE INVENTION

Accordingly, it is a primary object of the present invention to provide the means for preparing PB derived hematopoietic stem and progenitor cells in a novel and therapeutically more useful form. The product becomes a bag containing a high concentration of white blood cells having a high degree of cell viability.

A further object of the present invention is to provide a novel and useful method for generating the therapeutic product according to the previous object.

A further object of the present invention is to provide an aseptic and interconnected bag set for use in conjunction with the method of developing the therapeutic product hereinabove.

A further object of the present invention is to provide a freezer storage bag configured to contain the therapeutic dose in a cryoprotected environment for protracted periods of time until needed for dosage.

A further object of the present invention is to provide a freezer bag as noted above provided with a plurality of compartments in which the therapeutic dose has been sequestered so that various aliquots can be strategically excised from the freezer bag for several purposes.

Viewed from a first vantage point, it is an object of the present invention to provide a system for developing placental stem cells, comprising in combination: a first blood bag adapted to receive blood from a placenta therewithin, means within the blood bag to prevent coagulation, reagent means removably coupled to the blood bag, means for separating supernatant from the first blood bag and into a white cell bag, means for separating white cells from plasma in the white cell bag, a plasma bag removably coupled to the white cell bag for receiving the expressed plasma from the white cell bag, cryoprotectant means operatively coupled to the white cell bag, and a stem cell freezing bag operatively coupled to the white cell bag for transferring contents from the white cell bag to the stem cell freezing bag.

Viewed from a second vantage point, it is an object of the present invention to provide a method for preparing concentrated and partially purified white blood cell suspensions containing placental stem cells, comprising the steps of: placing blood from a placenta into a first blood bag, preventing coagulation within the blood bag, coupling reagent means into the blood bag, centrifuging and separating white blood cell rich supernatant from the first blood bag and placing the supernatant into a white cell bag, separating white cells from plasma in the white cell bag, removably coupling a plasma bag to the white cell bag and expressing the plasma from the white cell bag into the plasma bag. Coupling cryoprotectant means to the white cell bag, transferring contents from the white cell bag to a stem cell freezing bag, and freezing the stem cell freezing bag with its contents follows.

Viewed from a third vantage point, it is an object of the present invention to provide a therapeutic product comprising at least 80% of the white blood cells (including stem and progenitor cells) with viability greater than 90% and fewer than 10% of the red blood cells in the original PB collection.

These and other objects will be made manifest when considering the following detailed specification when taken in conjunction with the appended drawing figures.

BRIEF DESCRIPTION OF THE DRAWING FIGURES

DESCRIPTION OF PREFERRED EMBODIMENTS

Figure 1:
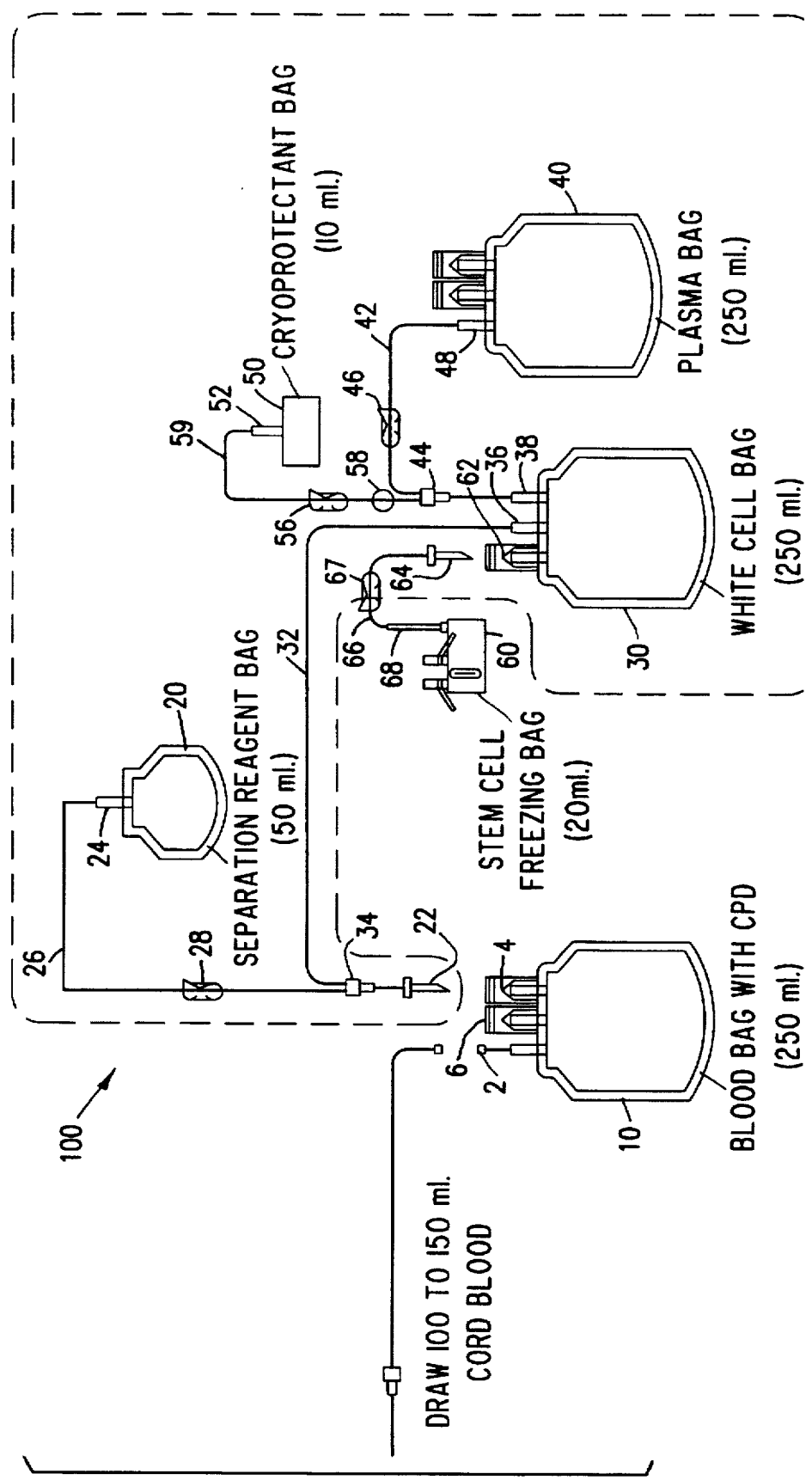
FIG. 1 is a schematic view of the stem cell processing bag set according to the present invention.
Figure 2:
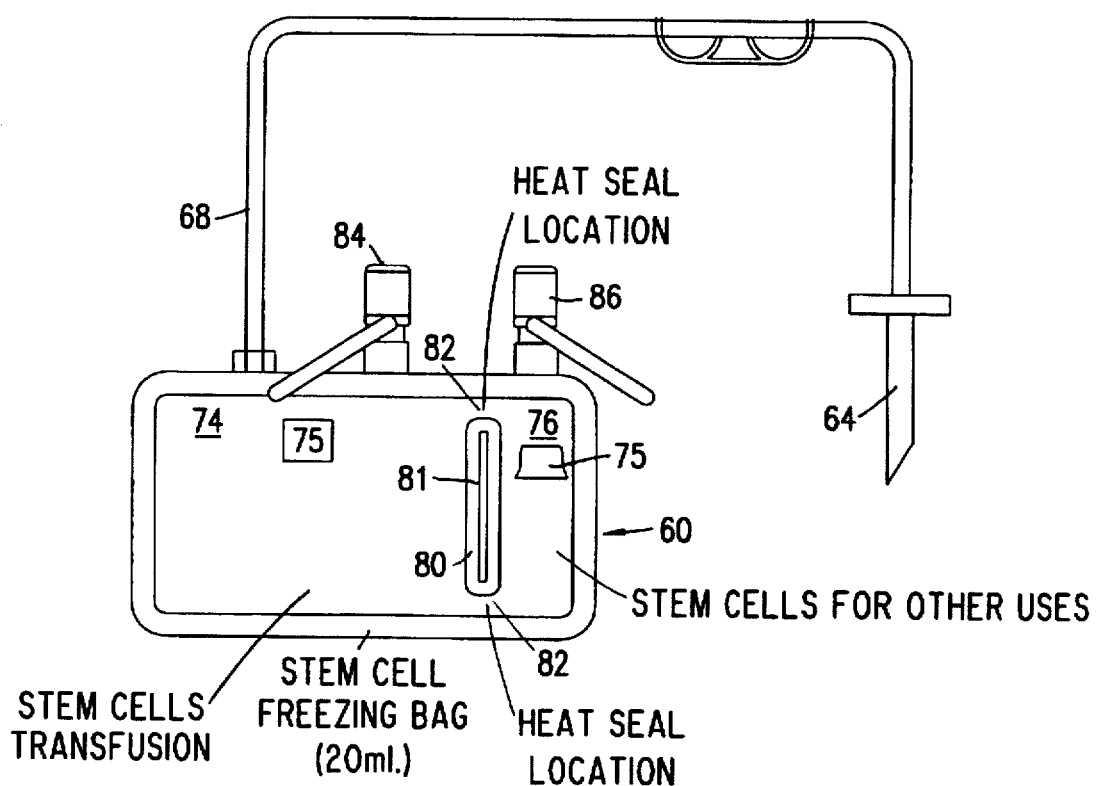
FIG. 2 is a detailed view of the freezing bag shown in FIG. 1.
Figure 3:
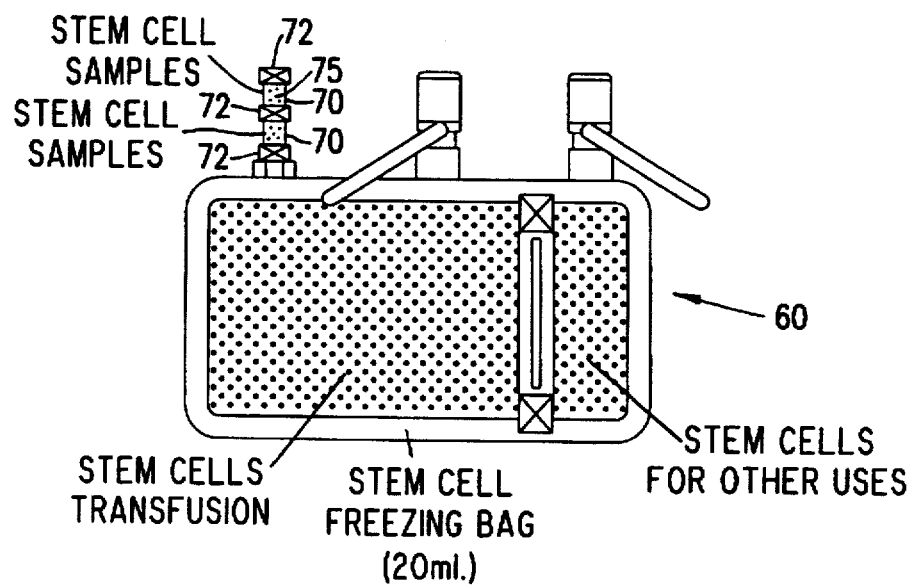
FIG. 3 is a view similar to FIG. 2 showing the interior of the freezing bag.
Figure 4:
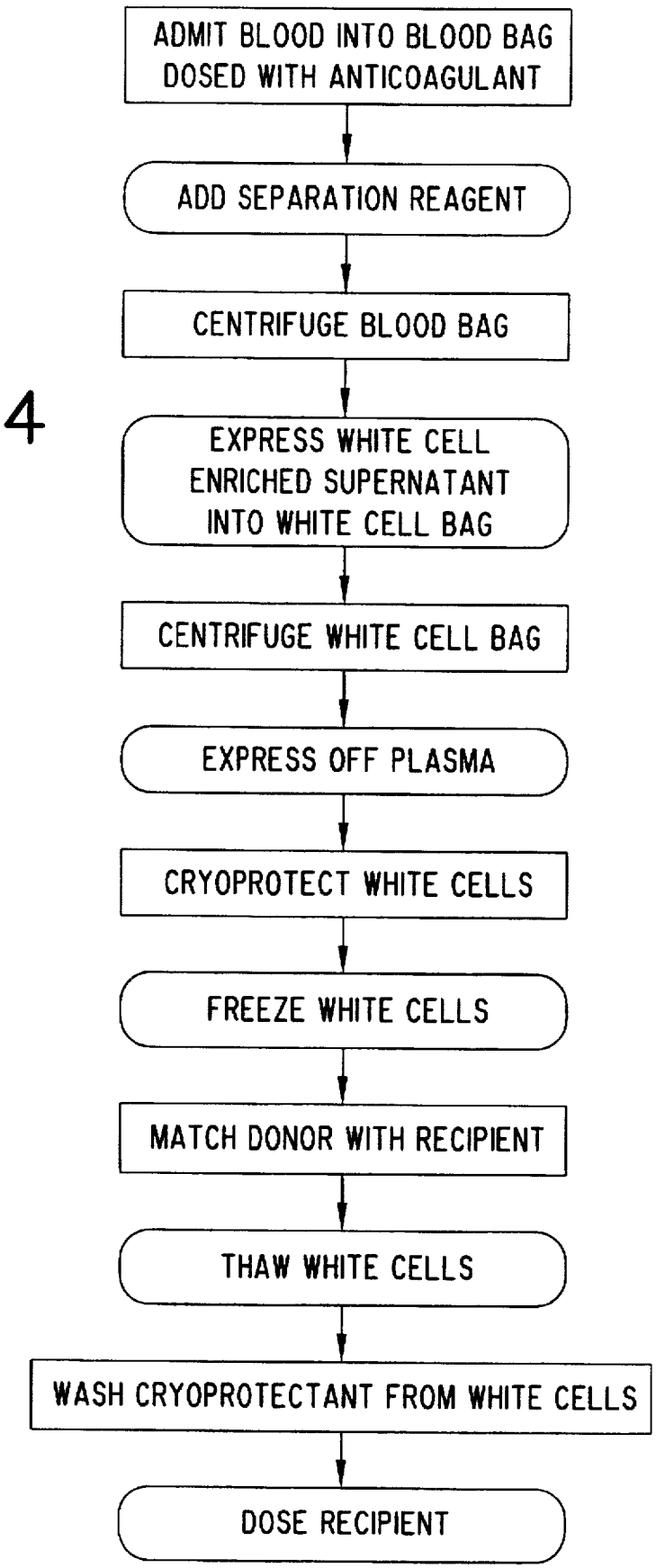
FIG. 4 is a flow chart the method according to the present invention.

Referring to the drawings now, wherein like reference numerals refer to like parts throughout various figures, reference numeral 100 is directed to an apparatus according to the present invention.

In essence, the apparatus 100 may be viewed as three arrays of bags collectively defining a bag set. Individual bags are provided with removable connection means to assure selected admission into the several bags only under aseptic conditions. In a preferred form of the invention, the array of bags 100 includes six bags: a blood bag 10 defining a first array; a reagent bag 20, a white cell bag 30, a plasma bag 40 and a cryoprotectant bag 50 defining a second array; and a stem cell freezing bag 60 defining a third array. Cord blood (i.e. blood from the placenta and umbilical cord) is admitted to the blood bag 10 which had previously been dosed with an anticoagulant. Next, the second array is connected to the blood bag 10. A separation reagent is admitted to the blood bag via conduit 26 from reagent bag 20. Centrifuging blood bag 10 follows. Supernatant containing the white blood cells is expressed off into the white cell bag 30, whereupon further centrifugation takes place. Next, supernatant plasma is expressed off into the plasma bag 40 leaving sedimented white blood cells in white cell bag 30. Cryoprotectant from the cryoprotectant bag 50 is transferred via conduit 59 to the white cell bag 30 slowly. Subsequently, the contents of the white cell bag 30 are transferred to the stem cell freezing bag 60 which is thereafter frozen and stored in liquid nitrogen for subsequent use.

More specifically, and with reference to FIG. 1, whole, placental, and umbilical cord blood is collected into a blood bag 10 provided with an anticoagulant such as Citrate, Phosphate and Dextrose (CPD). Assume, for the sake of explanation, that one hundred (100) milliliters of blood are placed within the blood bag. Typically, cord blood will exhibit a ratio of one thousand (1,000) red cells to each "non-red" cell (for simplicity, assume the non-red blood cell can be labeled white blood cells). Naturally, the main recognizable and functionally capable cells circulating in blood include erythrocytes, neutrophilic, eosinophilic, and basophilic granulocytes; B- T- and non B- non T-lymphocytes; monocytes and platelets. These mature cells derive from and are replaced, on demand, by morphologically recognizable dividing precursor cells for the respective lineages such as erythroblasts for the erythrocyte series, myeloblasts, promyelocytes and myelocytes for the granulocyte series, and megakaryocytes for the platelets. The precursor cells derive from more primitive cells that can simplistically be divided into two major subgroups: stem cells and progenitor cells. Of course, neonatal blood has other cellular constituents which will not be discussed here so as not to obscure the essence of the invention. The blood bag 10 includes at least two access portals. A first portal 2 receives the cord blood whereupon the access portal 2 is sealed. Typically sealing includes a heat seal to insure asepsis. A second portal 4 is provided which communicates with a spike 22 coupled via conduit 26 to a separation reagent bag 20 and through conduit 32 to the white cell bag 30 from the second array of bags discussed above. In addition, the blood bag 10 may also be provided with a third access 6 which may include a sample tube, should it be found desirable to place into storage an exemplar of the cord blood which was originally drawn. Access 6 may also provide alternative connections to bag 10.

Once the cord blood has been admitted into the blood bag 10, the admixture with an anticoagulant such as CPD prevents the clotting of the placental blood and readies the blood for admixture with a reagent contained within reagent bag 20. After the admission of the reagent to the blood bag and thorough mixing, the bag is centrifuged at a precise speed and the white-cell-rich supernatant is expressed into the white cell bag 30. The reagent is intended to facilitate the sedimentation of the red blood cells which is greatly accelerated by a very light centrifugation step (50×G ×5 min.). The effects of the addition of separation reagent and centrifugation are to produce a supernatant which contains eighty to ninety-five percent (80–95%) of the white blood cells and less than ten percent (10%) of the red blood cells of the originally collected blood. This reduces the presence of red cells (compared to white cells) by approximately ninety percent (90%). In the white cell bag, the red cell to white cell count ratio is now reduced to approximately one hundred (100) to one (1).

Typically, reagents which promote effective separation of the red blood cells from the white blood cells operate on the basis of mechanisms which can be the subject matter of some speculation as to the physical process or model that describes the separation process. One vantage point advances the premise that the addition of the reagent raises the dielectric strength of the suspension medium and then, its charge-dissipating capacity, so that the tendency for the red blood cells to remain in uniform suspension is disturbed. Another view is that the polymeric molecule of the reagent binds to two or more red blood cells, causing them to aggregate and form characteristic "rouleaux" i.e., loose clumps of red blood cells stacked together by the flat aspects of their discoidal surface. The effect, however, irrespective of the physical model that one envisions, is that separation between the red and white cells is possible with relatively minor, gentle and brief centrifugation. This accelerates the settling of the red cells and preserves the white cells in the suspended, unmodified state. In a preferred embodiment, once the reagent from bag 20 has been placed within the blood bag 10, centrifugation at fifty (50) gs for approximately five (5) minutes provides effective separation.

Reagents which change the charge dissipation characteristic or alter the dielectric strength of the constituent components can be selected from a relatively broad range of suitable substances. A six percent (6%) concentration of Heptastarch is presently preferred both due to efficacy, cost, and wide spread utilization in clinical blood processing. However, similar natural polymers such as dextrans, gelatins, modified or unmodified starches or synthetics such as polyethylene glycol or polyvinyl-pyrrolidone and many others could conceivably be substituted as conditions warrant. A similar effect may also be obtained with substances whose molecules attach with high avidity to two or more red cells such as antibodies and lectins. In any event, any one of these red cell-cryoprecipitating reagents contained in the reagent bag is dispensed from the reagent bag 20 via outlet 24 through branch passageway 26 and through the outlet spike 22 received by portal 4 or, alternatively, portal 6, into the blood bag 10.

Mixing of the reagent with the blood in the bag 10 followed by gentle centrifugation results in a separation in which the supernatant composed of plasma, most of the white blood cells and a small fraction of the red blood cells, is expressed off into the white cell bag 30 via a branch passageway 32 communicating between the spike 22 and the bag 30 with a T-adapter 34 which allows a bifurcation between the branch 26 and the branch 32. The bulk of the red blood cells remain in bag 10. The enriched white cell mixture is prevented from entering the reagent bag by means of a clamp 28 operatively engaged on the branch passage 26. The enriched white cell mixture in the white cell bag 30 at inlet 36 is now ready for further processing.

As an example, assume one hundred (100) milliliters of PB had been originally collected into blood bag 10. A preferred embodiment provides a reagent bag 20 with a sufficient volume of Hydroxyethyl starch (Heptastarch, Dupont) to provide for the addition of a volume equal to one-fifth (⅕) that of the PB collection into bag 10. In this example, one-fifth (⅕) of one hundred (100) milliliters equals twenty (20) milliliters. Typically, seventy (70) milliliters of white cell enriched supernatant plasma (containing the reagent solution) will be produced which will be expressed into the white cell bag 30. Once there, the contents are subjected to further centrifugation at four hundred (400) xGxten (10) minutes. Typically, of the seventy (70) milliliters that had been admitted into the white cell bag 30, fifty-five (55) milliliters will be expressed off thereafter into a plasma bag 40, leaving approximately fifteen (15) milliliters of highly-enriched white cell product in bag 30. The supernatant transferred to bag 40 contains the bulk of the plasma, anticoagulant and reagent and essentially no cells.

The white cell bag 30 includes an outlet portal 38 that communicates with the plasma bag 40 via a branch conduit 42 having a T-adapter 44 and a constrictor 46 in line. The supernatant is expressed from white cell bag 30 via conduit 42 to the plasma bag 40 via its own portal 48. Once the supernatant has been received into the plasma bag 40 it is sealed off and the plasma bag 40 is disconnected from the white cell bag 30.

Cryoprotectant from cryoprotectant bag 50 is next admitted into the white cell bag 30. Cryoprotectant bag 50 includes an outlet 52, a branch passageway 54 and a constrictor element 56 on the line 54 in fluidic communication with the portal 38 of the white cell bag 30 through T-adapter 44. Typically, three point eight (3.8) milliliters of cryoprotectant is admitted into the fifteen (15) milliliters contained within the white cell bag 30. It is extremely desirable to admit the cryoprotectant into the white cell bag 30 at a relatively slow rate. Typically, the three point eight (3.8) milliliters of cryoprotectant is admitted into the bag over a twenty (20) minute interval, while continuously mixing the cryoprotectant with the contents of the white cell bag by hand or with an orbital shaker. A preferred cryoprotectant solution includes Dimethyl Sulfoxide DMSO (an intracellular cryoprotectant) diluted to fifty percent (50%) with dextran an extracellular cryoprotectant. One feature of the instant invention is that the constrictor element 56 determines that the intracellular cryoprotectant can only enter white cell bag 30 very slowly. Thus, the intracellular cryoprotectant increases its concentration and permeates the white cell mixture contained within the white cell bag 30 without causing damage to the cells. In order to effect same, a metering instrumentality 58 may be interposed in the branch 54 instead of the constrictor element 56 (should the constriction not provide a constant flow rate) and in fluid communication with the portal 38. The metering instrumentality 58 can be a pump. Alternatively the cryoprotectant bag and pump arrangement can be replaced with a syringe or other metering apparatus which facilitates the slow addition of cryoprotectant to the white cell bag 30.

The physical analogy for the cryoprotectant is that the DMSO penetrates through the white cell membrane and reduces the capacity of intracellular water as it freezes to crystallize intracellularly and inflict damage to the cell walls. Dextran and other extracellular cryoprotectants such as diverse kinds of soluble starches, proteins and sugars are believed to provide extracellular layers around white cells that insulate the cells from the tendency of the water to form crystals during the freezing process and to develop excessive extracellular hyperosmolarity, both of which might reduce cell wall integrity and cellular viability. By providing the cryoprotectant at a measured rate, over a relatively long period of time, cell viability will have been maximized by providing ample time for the DMSO to diffuse into cells and to reach equilibrium across the cell membrane and for the dextran to be homogeneously diluted in the surrounding plasma.

As an example of the preferred embodiment, three and eight/tenth (3 and 8/10) milliliters of cryoprotectant is added to the fifteen (15) milliliters of white cells in the white cell bag 30. This addition brings the concentration of DMSO to ten percent (10%) in bag 30. White cell bag 30 has another outlet 62 which receives a spike 64 from the stem cell freezing bag 60 in an aseptic manner. The white cell bag 30 communicates with stem cell freezing bag 60 via conduit 66 controlled by clamp 67. The cryoprotected white cell mixture is received into the stem cell freezing bag 60 via portal 68. The portal 68 is specially configured to include a stand tube which allows a standing column of stem cell mixture to be retained therewithin for sequestering into a series of compartments 70, each spaced from the other by heat seals 72. These specimens 70 can be used for pre-infusion confirmation of an optimum HLA match or other tests, once a particular stem cell freezing bag 60 has been chosen as appropriate for the putative recipient.

The stem cell freezing bag 60 is further characterized by having a plurality of compartments within the main body of the bag 60, each compartment provided with indicia 75 thereon for identification of the specific unit, establishing a form of chain of custody. More particularly, the stem cell freezing bag 60 includes at least a first major portion 74 and a second minor portion 76. Typically, the ratio between the major portion 74 and the minor portion 76 is eighty percent (80%) major portion and twenty percent (20%) minor portion. These portions of bag 60 are delimited by heat seal 80 and, after filling, contribute to dividing the stem cell freezing bag into two, intimately attached, but independent white cell containers once heat seals at both locations 82 are executed.

Each portion is in communication with its own outlet. The major portion 74 is in communication with its portal 84 while the minor portion 76 communicates with its own portal 86. In addition, the heat seal location may include a line of demarcation 81 defining a scoreline which allows the major portion 74 to be severed, without thawing, from the minor portion 76. It is contemplated that the stem cells contained in the minor portion 76 can be allocated for other uses, such as for increasing the numbers of useful cells by culturing the stem and progenitor cells in a propagation medium. The stem cells in major portion 74 are left undisturbed for administration as transplants. The freezer bag 60 and stand tube/portal 68 have negligible thickness. The purpose of this particular geometry is to assure that the white cells in compartments 76, 74 and 70 all maintain a uniform and narrow thickness so that subsequent freezing regimens achieve near identical controlled rate freezing conditions.

In a preferred embodiment, approximately nineteen (19) milliliters of therapeutic product are contained within the freezing bag 60. The stem cell freezing bag 60 is gradually frozen to an extremely low temperature such as in liquid nitrogen for permanent storage. This preserves the stem cells in a state such that, upon thawing, they are recovered in quantity and exhibit a high degree of cell viability.

Once it has been determined that the given stem cells within a freezing bag 60 are to be used in a transplant procedure, the stem cells are first thawed to a temperature where the stem cells and constituent components change phase back from a solid to a liquid. Next, the stem cells are washed to remove the cryoprotectant which was added prior to freezing. Preferably, the wash is intended to remove the DMSO by using an isotonic fluid, preferably a colloid. For example, a mixture having five percent (5%) albumin and ten percent (10%) dextran in a saline solution is used to dilute the DMSO in the extracellular environment and secondarily reduce its concentration inside the white blood cells. Subsequently, the mixture is centrifuged at four hundred (400) gs for ten (10) minutes with the supernatant expressed therefrom.

As mentioned supra, the enriched white cells were present in volume at approximately fifteen (15) milliliters prior to the addition of three point eight (3.8) milliliters of cryoprotectant. When placed in the stem cell freezing bag, about four (4) milliliters were placed in the secondary compartment 76 and fifteen (15) milliliters were retained in the primary container 74. In actuality, somewhat less than the four (4) milliliters are allocated as is just described because the stem cell samples contained within compartments 70 may contain collectively up to one (1) milliliter. In any event, the thawed white blood and stem cell suspension prior to washing contained ten (10%) cryoprotectant by volume. After the dilution, spinning and expressing off the supernatant the sedimented stem cells (typically in a volume less than three (3) milliliters) are diluted once again to a volume adequate for administration to the recipient, fifteen (15) milliliters or more. This second dilution reduces the concentration of DMSO to below one percent (1%). Therefore, the quantity of DMSO retained is in the order to one-tenth (1/10) gram. This is very much less, compared with the prior art which typically may have involved two hundred (200) milliliters of ten percent (10%) DMSO i.e. twenty (20) grams of this compound.

In addition, the therapeutic dose described in the disclosed invention hereinabove has a special efficacy because the processing described hereinabove has removed from the whole blood, the bulk of the red cells, plasma, cryoprotectant, free hemoglobin, etc. which heretofore have exhibited adverse consequences on the recipient and has restored the osmolarity of the stem and progenitor cells to the normal range of three hundred (300) milliosmols from the over one thousand (1000) milliosmols of ten percent (10%) DMSO solution.

It is to be noted that the stem cells that are stored in freezing bags must be kept at extremely low temperatures such as those achievable using liquid nitrogen. By providing white stem cells in twenty (20) milliliter quantities, the problems that would have existed before in the provision of storage space for units with ten fold larger volumes of cryopreserved placental blood (whole) will have been solved by the smaller storage requirement of separated white blood cells associated with the instant invention.

One attribute of the instant invention is that the therapeutic dose involves a relatively low level of DMSO in the finished product that is to be administered. A second attribute involves the fact that a ten (10) fold lower concentration of red blood cells are contained in a unit without significant loss of stem and progenitor cells. The lower red blood cell numbers reduce the presence of hemoglobin in the thawed specimen and decrease the problems associated with red blood cell incompatibilities. Further, the viability of the white cells contained in the dose after thawing is typically three (3) to four (4) fold higher than in the prior art, particularly after administration and dilution in the recipient's own plasma. Experimentally, thawed white cells are diluted in twenty (20) milliliters of plasma prior to counting for viability. In prior art, unwashed white cell viability was typically of the order of twenty percent (20%). According to the present invention, using the DNA fluorescence stain or other viability tests, the mononuclear cells are much greater than twenty percent (20%), typically greater than ninety percent (90%) viable. When stem and progenitor cells are cultured in vitro from such white cell concentrates after thawing as described, the number of viable cells estimated by the number of colonies formed is also greater than ninety percent (90%) of the original numbers.

While the previous discussion has focused on the desirability of using cord blood from placental stem cells, other peripheral stem cells can also be processed in a similar manner to provide benefits. Further, having thus described the invention it should be apparent that numerous structural modification and adaptations of the bag set, the chemical nature of the reagents and cryoprotectants and the details of the processing steps, may be resorted to without departing from the scope and fair meaning of the instant invention as set forth hereinabove and as described hereinbelow by the claims.

I claim:

1. A method for concentrating white blood cells contained in placental, umbilical cord and/or peripheral donor blood which has been contacted with an anticoagulant to prevent coagulation of said donor blood, said method comprising performing the following sequential steps in a series of removably coupled, interconnected bags under aseptic conditions:

centrifuging said anticoagulated blood in a blood bag in the presence of a red blood cell sedimentation reagent at a speed sufficient to obtain a first sediment and a first supernatant, wherein said first sediment comprises at least 90% of red blood cells contained in said anticoagulated blood and said first supernatant comprises at least 80% of white blood cells contained in said anticoagulated blood and wherein said speed is about 50×G;

introducing said first supernatant into a white cell bag;

centrifuging said white cell bag to obtain a second sediment and a second supernatant; and removing all or a portion of said second supernatant so as to retain in said white cell bag a composition comprising at least 80% of white blood cells contained in said donor blood, less than 10% of red blood cells contained in said donor blood, and less than all of plasma contained in said donor blood.

2. The method of claim 1, wherein said sedimentation reagent comprises hydroxyethyl starch.

3. The method of claim 1, which further comprises contacting said composition with a cryoprotectant at a rate and an amount sufficient to obtain a cryoprotected composition without damaging cells contained in said composition; and freezing said cryoprotected composition.

4. The method of claim 3, wherein said cryoprotectant comprises dimethylsulfoxide.

5. The method of claim 4, wherein said cryoprotectant further comprises dextran.

6. The method of claims 4, wherein the final concentration of dimethylsulfoxide in the cryoprotected composition is 10%.

7. The method of claim 1, wherein the donor blood is placental blood.

8. The method of claim 1, wherein the donor blood is umbilical cord blood.

9. The method of claim 1, wherein the donor blood is peripheral blood.

* * * * *